US012572897B2

(12) United States Patent (10) Patent No.: US 12,572,897 B2
Maeda et al. (45) Date of Patent: Mar. 10, 2026

(54) WORK MANAGEMENT DEVICE, WORK MANAGEMENT METHOD, AND RECORDING MEDIUM

(71) Applicant: NEC Corporation, Tokyo (JP)

(72) Inventors: Kazuki Maeda, Tokyo (JP); Hiroko Imai, Tokyo (JP); Mitsuhiro Nakayama, Tokyo (JP)

(73) Assignee: NEC CORPORATION, Tokyo (JP)

( * ) Notice: Subject to any disclaimer, the term of this patent is extended or adjusted under 35 U.S.C. 154(b) by 146 days.

(21) Appl. No.: 18/371,652

(22) Filed: Sep. 22, 2023

(65) Prior Publication Data

US 2024/0112146 A1 Apr. 4, 2024

(30) Foreign Application Priority Data

Sep. 29, 2022 (JP) ................................. 2022-155665

(51) Int. Cl.
G06Q 10/1091 (2023.01)
G16H 40/20 (2018.01)
(52) U.S. Cl.
CPC ......... *G06Q 10/1091* (2013.01); *G16H 40/20* (2018.01)
(58) Field of Classification Search
CPC ............................ G06Q 10/1091; G16H 40/20
See application file for complete search history.

(56) References Cited

U.S. PATENT DOCUMENTS

| | | | | |
|---|---|---|---|---|
| 8,463,670 B2 * | 6/2013 | Chaar | ................ | G06Q 10/0639 |
| | | | | 714/39 |
| 9,070,119 B2 * | 6/2015 | Catipon, Jr. | ......... | G06Q 10/109 |
| 9,396,232 B1 | 7/2016 | Kapoor et al. | | |
| 10,679,158 B2 * | 6/2020 | Bares | ............. | G06Q 10/063116 |
| 2003/0040925 A1 | 2/2003 | Gutta et al. | | |
| 2003/0225989 A1 * | 12/2003 | Licalsi | ................... | G06Q 30/04 |
| | | | | 711/167 |
| 2006/0284838 A1 * | 12/2006 | Tsatalos | ................ | G06Q 10/10 |
| | | | | 345/156 |

(Continued)

FOREIGN PATENT DOCUMENTS

| | | |
|---|---|---|
| JP | 2007-257429 A | 10/2007 |
| JP | 4251374 B1 | 4/2009 |

(Continued)

OTHER PUBLICATIONS

Kasliwal, Sonal, Sushma Kotkar, and H. D. Gadade. "Employee Tracking and Monitoring System Using Android." International Journal of Innovative Research in Advanced Engineering (IJIRAE) (2016): 1-4. (Year: 2016).*

(Continued)

*Primary Examiner* — Nathan A Mitchell
(74) *Attorney, Agent, or Firm* — Sughrue Mion, PLLC

(57) ABSTRACT

Provided is a work management device including an acquisition unit that acquires information indicating login to a system using a first terminal and an operation history of the first terminal occurring after login to the system, a specifying unit that specifies a non-operation period of a terminal from the operation history of the first terminal, and a calculation unit that calculates working hours including the non-operation period of the terminal according to a length of the non-operation period of the terminal.

11 Claims, 9 Drawing Sheets

(56) References Cited

U.S. PATENT DOCUMENTS

| | | | |
|---|---|---|---|
| 2007/0094110 A1* | 4/2007 | McCrea | G06Q 30/04 705/32 |
| 2007/0112654 A1* | 5/2007 | Garcia | G06Q 10/1091 702/187 |
| 2008/0027778 A1* | 1/2008 | Srinivasan | G06Q 50/10 705/7.13 |
| 2009/0248553 A1 | 10/2009 | Taylor et al. | |
| 2010/0157062 A1 | 6/2010 | Baba et al. | |
| 2013/0297468 A1* | 11/2013 | Hirsch | G06Q 10/109 705/32 |
| 2013/0317836 A1* | 11/2013 | Wons | G06Q 10/1091 705/2 |
| 2014/0188577 A1* | 7/2014 | Gerber | G06Q 10/1091 705/7.42 |
| 2014/0258057 A1* | 9/2014 | Chen | G06Q 10/105 705/32 |
| 2014/0310139 A1* | 10/2014 | Cornet | G06Q 10/1091 705/32 |
| 2015/0081487 A1* | 3/2015 | Porter | G06Q 10/1091 705/32 |
| 2015/0327011 A1* | 11/2015 | Fairbanks | G01S 5/013 455/456.3 |
| 2016/0306965 A1* | 10/2016 | Iyer | G06Q 10/0635 |
| 2017/0169520 A1* | 6/2017 | Cornet | G06Q 40/125 |
| 2017/0351906 A1 | 12/2017 | Oguchi et al. | |
| 2018/0040178 A1 | 2/2018 | Nagata et al. | |
| 2018/0211724 A1 | 7/2018 | Wang | |
| 2019/0057340 A1* | 2/2019 | Wang | G06Q 10/109 |
| 2020/0357210 A1 | 11/2020 | Ishiyama | |
| 2021/0051166 A1* | 2/2021 | Niazi | G06F 16/1734 |
| 2022/0215347 A1* | 7/2022 | Peres | G06N 3/045 |
| 2022/0215348 A1 | 7/2022 | Tanno | |
| 2023/0293134 A1 | 9/2023 | Horiuchi et al. | |
| 2023/0298738 A1 | 9/2023 | Ho et al. | |
| 2024/0257063 A1* | 8/2024 | Sutton | G16Z 99/00 |
| 2025/0013985 A1 | 1/2025 | McCormick | |

FOREIGN PATENT DOCUMENTS

| | | |
|---|---|---|
| JP | 2017-079025 A | 4/2017 |
| JP | 2019-169034 A | 10/2019 |
| JP | 2019-169035 A | 10/2019 |
| JP | 2021-163233 A | 10/2021 |
| JP | 2022-031874 A | 2/2022 |
| WO | 2016/079827 A1 | 5/2016 |

OTHER PUBLICATIONS

Japanese Office Action for JP Application No. 2022-155665, mailed on Aug. 22, 2023 with English Translation.

JP Office Communication for JP Application No. 2022-155665, mailed on Feb. 20, 2024 with English Translation.

JP Office Action for JP Application No. 2022-155665, mailed on Oct. 31, 2023 with English Translation.

US Office Action for U.S. Appl. No. 18/394,079, mailed on Jul. 22, 2025.

Barabanshchikova, N., and N. Silkina. "Automatic Accounting of Working Hours in Small and Medium Enterprises." 2019 International Multi-Conference on Industrial Engineering and Modern Technologies (FarEastCon). IEEE, 2019. (Year: 2019).

US Office Action for U.S. Appl. No. 18/397,040 mailed on Jul. 18, 2025.

Yuganthini, P., et al. "Activity tracking of employees in industries using computer vision." 2021 5th International Conference on Trends in Electronics and Informatics (ICOEI). IEEE, 2021. (Year: 2021).

Yang, Ming, and Kai Yu. "Real-time clothing recognition in surveillance videos." 2011 18th IEEE international conference on image processing. IEEE, 2011. (Year: 2011).

* cited by examiner

Fig. 7

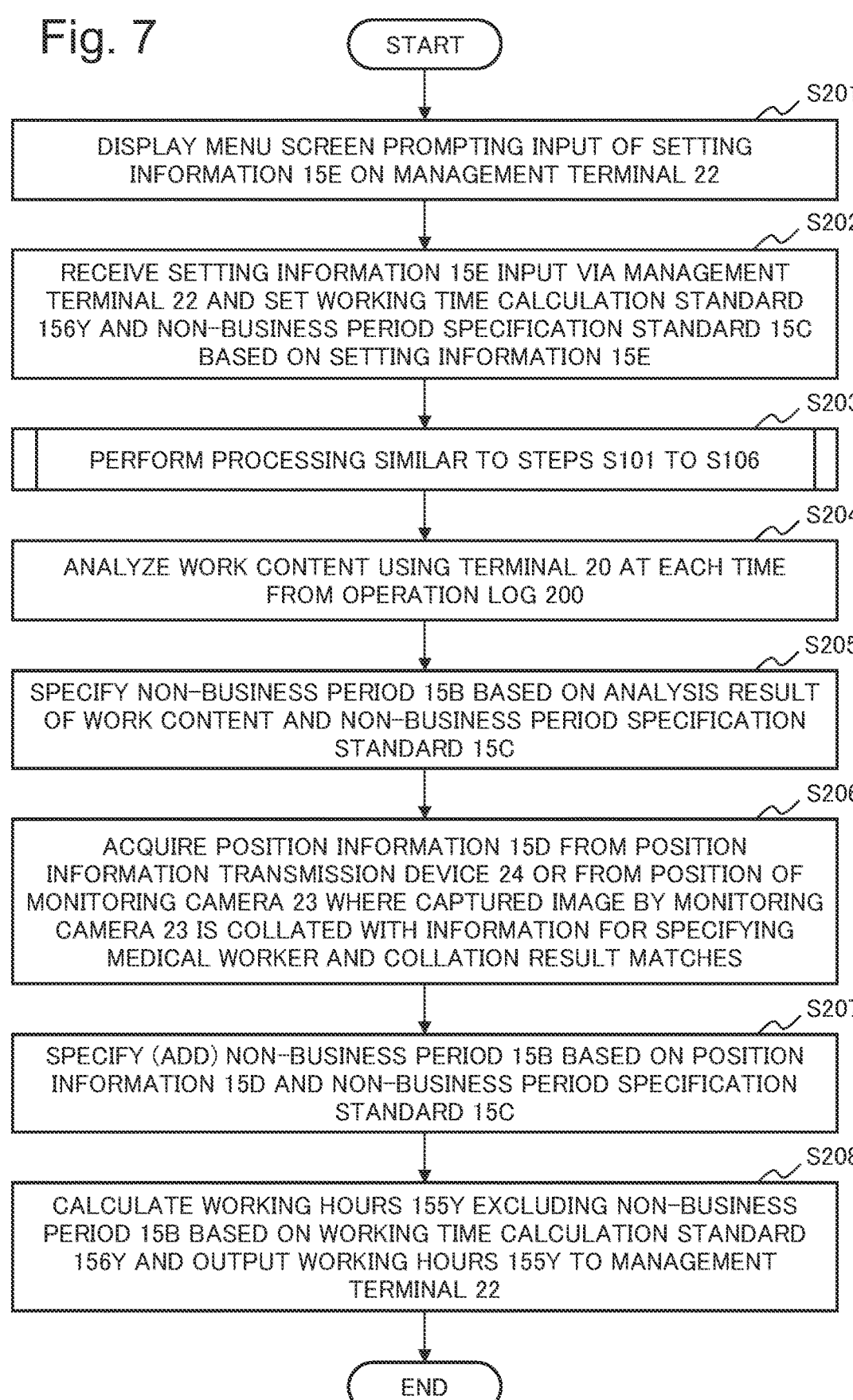

START

S201
DISPLAY MENU SCREEN PROMPTING INPUT OF SETTING INFORMATION 15E ON MANAGEMENT TERMINAL 22

S202
RECEIVE SETTING INFORMATION 15E INPUT VIA MANAGEMENT TERMINAL 22 AND SET WORKING TIME CALCULATION STANDARD 156Y AND NON-BUSINESS PERIOD SPECIFICATION STANDARD 15C BASED ON SETTING INFORMATION 15E

S203
PERFORM PROCESSING SIMILAR TO STEPS S101 TO S106

S204
ANALYZE WORK CONTENT USING TERMINAL 20 AT EACH TIME FROM OPERATION LOG 200

S205
SPECIFY NON-BUSINESS PERIOD 15B BASED ON ANALYSIS RESULT OF WORK CONTENT AND NON-BUSINESS PERIOD SPECIFICATION STANDARD 15C

S206
ACQUIRE POSITION INFORMATION 15D FROM POSITION INFORMATION TRANSMISSION DEVICE 24 OR FROM POSITION OF MONITORING CAMERA 23 WHERE CAPTURED IMAGE BY MONITORING CAMERA 23 IS COLLATED WITH INFORMATION FOR SPECIFYING MEDICAL WORKER AND COLLATION RESULT MATCHES

S207
SPECIFY (ADD) NON-BUSINESS PERIOD 15B BASED ON POSITION INFORMATION 15D AND NON-BUSINESS PERIOD SPECIFICATION STANDARD 15C

S208
CALCULATE WORKING HOURS 155Y EXCLUDING NON-BUSINESS PERIOD 15B BASED ON WORKING TIME CALCULATION STANDARD 156Y AND OUTPUT WORKING HOURS 155Y TO MANAGEMENT TERMINAL 22

END

Fig. 9

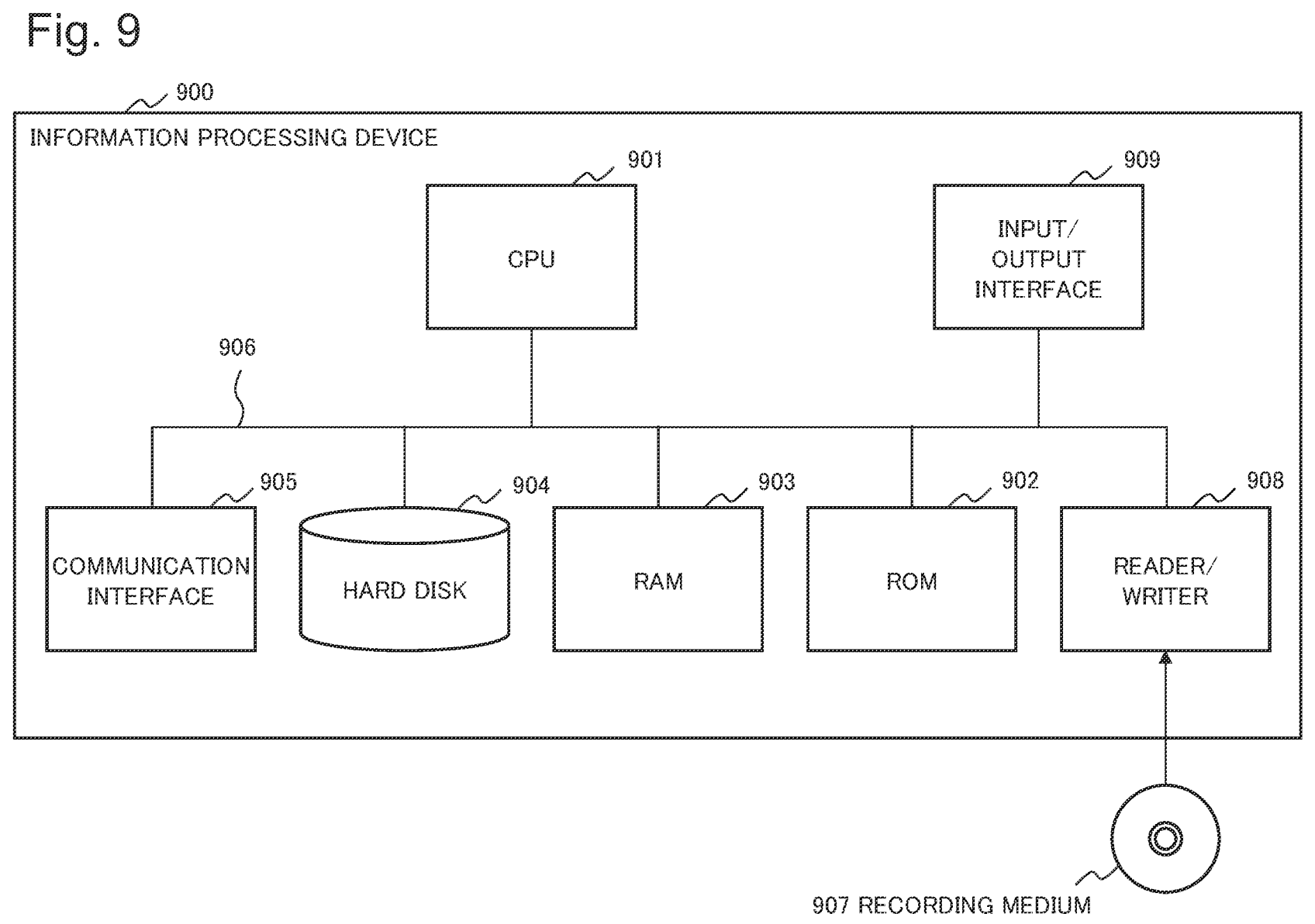

INFORMATION PROCESSING DEVICE 900

901 CPU

906

909 INPUT/OUTPUT INTERFACE

908 READER/WRITER

902 ROM

903 RAM

904 HARD DISK

905 COMMUNICATION INTERFACE

907 RECORDING MEDIUM

WORK MANAGEMENT DEVICE, WORK MANAGEMENT METHOD, AND RECORDING MEDIUM

This application is based upon and claims the benefit of priority from Japanese Patent Application No. 2022-155665, filed on Sep. 29, 2022, the disclosure of which is incorporated herein in its entirety by reference.

TECHNICAL FIELD

The present disclosure relates to a work management device, a work management method, and a recording medium.

BACKGROUND ART

There is known a technique for efficiently grasping working hours (actual working conditions) of a worker by utilizing an operation history of a terminal used during work, an access history to a system, and the like.

In relation to the above-described technology, Patent Literature 1 (JP 2019-169035 A) discloses a management system that supports objective business management. This system detects a login operation and a logoff operation in an information processing terminal. This system detects an operation input via an input unit in the information processing terminal. This system calculates a use time of the information processing terminal by a user based on the detection content described above. Then, this system displays a difference between the calculated use time and predetermined working hours on a display unit.

Patent Literature 2 (JP 2007-257429 A) discloses a working time calculation method for storing, for each of all accesses made to each electronic medical record in an electronic medical record system, a login date and time and a logout date and time in the access and business type information indicating a type of business of a staff who has made the access in association with each other. In this method, business type information and work area information for specifying a work area in which the business is performed are stored in association with each other. In this method, when a user enters an examination room, a working time from the entry to the access to the electronic medical record and an access period to the electronic medical record are counted as a unit working time of a diagnosis and treatment department associated with the examination room. Then, according to this method, when the user accesses the electronic medical record as a doctor of a second diagnosis and treatment department different from the first diagnosis and treatment department associated with the examination room, the access period is counted as a unit working time of the second diagnosis and treatment department.

In Patent Literatures 1 and 2 described above, the working hours of the worker are managed by detecting a login operation and a logoff operation to the system. However, there is a case where a busy worker finishes business without performing a logoff operation, for example. In such a case, the logoff operation cannot be detected. Therefore, the techniques of Patent Literatures 1 and 2 cannot accurately grasp the working hours of the worker.

An object of the present disclosure is to grasp working hours of a worker even accurately and easily when an input operation for grasping an end time of work is not performed.

SUMMARY

According to an aspect of the present disclosure, there is provided a work management device including an acquisition unit that acquires information indicating login to a system using a first terminal and an operation history of the first terminal occurring after login to the system, a specifying unit that specifies a non-operation period of a terminal from the operation history of the first terminal, and a calculation unit calculates working hours including the non-operation period of the terminal according to a length of the non-operation period of the terminal.

According to another aspect of the present disclosure, there is provided a work management method including, by an information processing device, acquiring information indicating login to a system using a first terminal and an operation history of the first terminal occurring after login to the system, specifying a non-operation period of a terminal from the operation history of the first terminal, and calculating working hours including the non-operation period of the terminal according to a length of the non-operation period of the terminal.

According to still another aspect of the present disclosure, there is provided a non-transitory recording medium storing a program for causing a computer to execute an acquisition process of acquiring information indicating login to a system using a first terminal and an operation history of the first terminal occurring after login to the system, a specifying process of specifying a non-operation period of a terminal from the operation history of the first terminal, and a calculation process of calculating working hours including the non-operation period of the terminal according to a length of the non-operation period of the terminal.

BRIEF DESCRIPTION OF THE DRAWINGS

Exemplary features and advantages of the present disclosure will become apparent from the following detailed description when taken with the accompanying drawings in which:

FIG. 7 is a flowchart illustrating an operation of a work management device according to the present disclosure;

FIG. 9 is a block diagram illustrating a configuration of an information processing device capable of achieving the work management device according to each example embodiment of the present disclosure.

EXAMPLE EMBODIMENT

Figure 1:
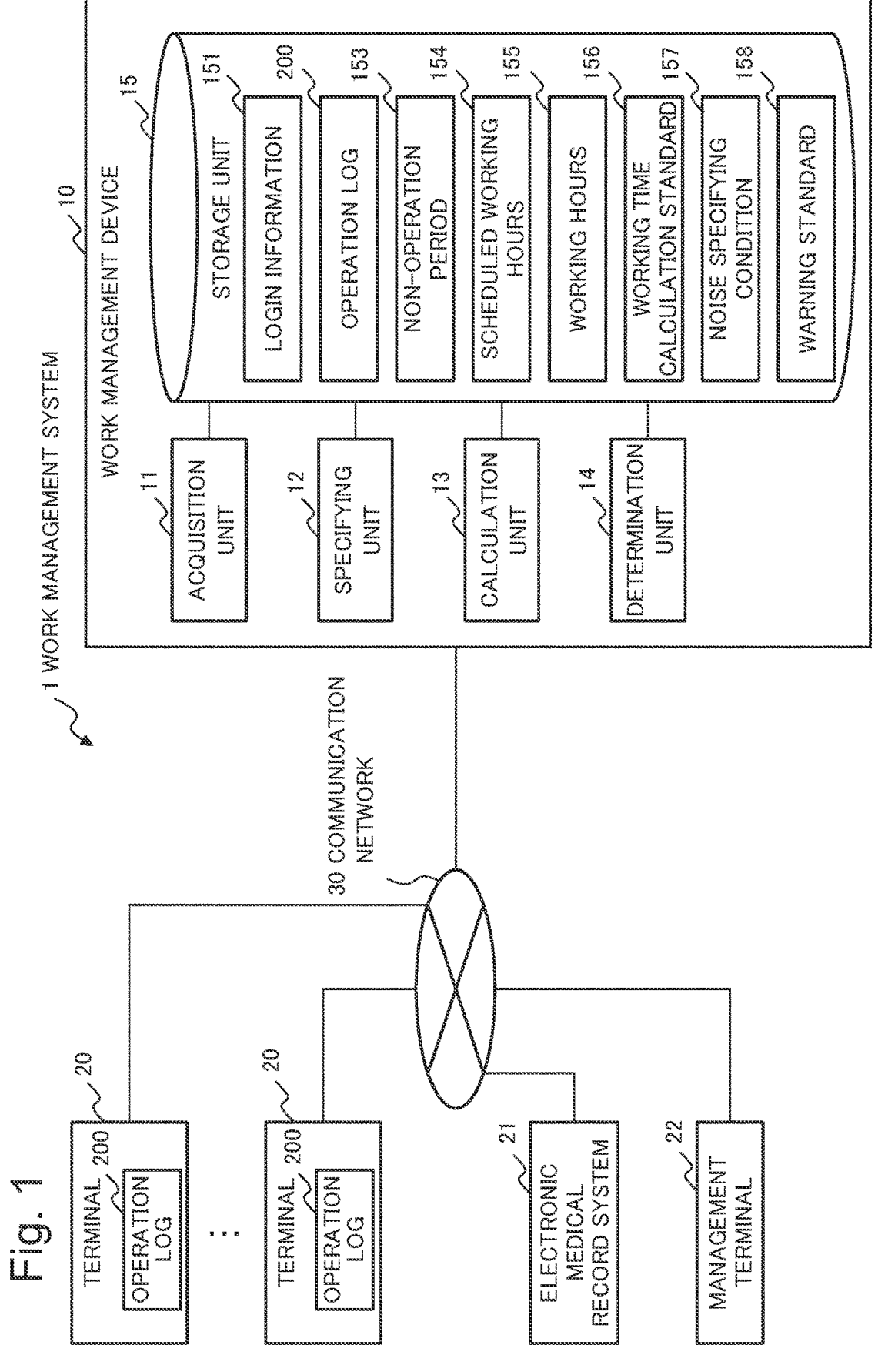
FIG. 1 is a block diagram illustrating a configuration of a work management system according to the present disclosure.

Example embodiments of the present disclosure will be described below with reference to the drawings. In the following example embodiments, technically preferable limitations are imposed to carry out the present disclosure, but the scope of this invention is not limited to the following description. In all drawings used to describe the following example embodiments, the same reference numerals denote similar parts unless otherwise specified. In addition, in the following example embodiments, a repetitive description of similar configurations or arrangements and operations may be omitted.

First Example Embodiment

FIG. 1 is a block diagram illustrating a configuration of a work management system 1 according to a first example embodiment of the present invention. The work management system 1 is a system that manages working hours of a medical worker such as a doctor or a nurse in a medical institution. The working hours to be managed by the work management system (work management device) according to the present example embodiment and other example embodiments to be described later are not limited to the medical worker, and may be a worker other than the medical worker who operates terminals during work.

The work management system 1 roughly includes a work management device 10, one or more terminals 20, an electronic medical record system 21, and a management terminal 22. The work management device 10, the terminal 20, the electronic medical record system 21, and the management terminal 22 are communicably connected via a communication network 30. The communication network 30 is, for example, a local area network (LAN) constructed in a medical institution, a virtual private network (VPN) constructed on the Internet, or the like. The work management system 1 may include a system for medical business different from the electronic medical record system 21.

The electronic medical record system 21 is a database related to medical care information, and the medical care information indicates patient attributes (name, gender, age, address), disease names and main symptoms, treatment methods (formulation, treatment), and dates of medical care. The medical care information may include a medical history, current symptoms, and physical findings regarding the patient, a course after hospitalization, a treatment policy, a surgical record, and the like.

The electronic medical record system 21 also has a function of instructing a medical worker such as a nurse or a pharmacist to perform an examination or the like from a doctor, a function of managing work progress, a function of transmitting and recording an examination result of a patient, and a function of calculating a medical treatment fee. The electronic medical record system 21 also has a function of supporting creation of medical documents (documents upon admission, letter of introduction, or the like). The electronic medical record system 21 also has a function of managing a nursing care plan, a care implementation status, and a progress status regarding a patient.

The electronic medical record system 21 also has a function of sharing medical care information and exchanging introduction letters among a plurality of medical institutions.

The terminal 20 is an information processing device such as a personal computer used by a medical worker during work, and is used, for example, when performing the above-described business using the electronic medical record system 21. The terminal is installed for each place such as an examination room and an operation room (work room), and is used by a medical worker who performs medical practice in the examination room, the operation room, or the like. The terminal 20 is not limited to a mode of being installed in a specific work room, and may be a mobile terminal such as a smartphone that can be carried to various work rooms. Therefore, the individual terminals are shared and used by one or more medical workers. Similarly, during work, an individual medical worker can use one or more terminals 20. In the present example embodiment, in the following description, the terminals 20 may be distinguished and described as a terminal 20-1 and a terminal 20-2.

The terminal 20 executes an application for collecting the operation log 200 after an operating system (OS) is activated and becomes ready for use by the medical worker. Then, the application collects the operation log 200 generated when the terminal 20 is operated. The operation log 200 includes the content of the operation via the terminal and the time of the operation. The operation log 200 is associated with an identification (ID) for identifying individual medical workers. This ID may be acquired from information input when the medical worker performs a login operation to the electronic medical record system using the terminal 20. Examples of the input information include, in addition to an ID given to each user of the electronic medical record system, information for identifying individual medical workers such as an employee number and an employee name. The timing of acquiring the input information is not limited to when the login operation is performed, and may be acquired after a lapse of a predetermined time or more after the login operation is performed. The login operation is performed at least one of when the medical worker starts using the terminal 20 and when the medical worker starts accessing the electronic medical record system 21 from the terminal 20. One medical worker may perform a login operation using the terminal 20 a plurality of times during working hours. Similarly, one medical worker may log in using the terminal 20-1 different from the terminal 20 during working hours. Furthermore, login may be performed simultaneously using the terminal 20 and the terminal 20-1.

The operation log 200 includes, for example, identification information (terminal name or the like) of the terminal 20, information indicating movement of a mouse, information (characters or the like) input via a keyboard, identification information (name or the like) of an application or a file to be operated, a type of operation (save, overwrite, delete, or the like) performed on the application or the file, a start time of the operation, an end time of the operation, or the like. The operation log 200 may acquire information obtained by combining all or some of pieces of the above-described information as the operation log 200, or may include information different from the above-described information. The operation log 200 may include at least an operation start time or an operation end time in order to specify a non-operation period to be described later.

The management terminal 22 is an information processing device such as a personal computer used by an administrator of the work management device 10, and is used, for example, when inputting information to the work management device 10 and when confirming information output from the work management device 10. At least one of the terminals 20 may have a function as the management terminal 22.

The work management device 10 includes an acquisition unit 11, a specifying unit 12, a calculation unit 13, a determination unit 14, and a storage unit 15. The acquisition unit 11, the specifying unit 12, the calculation unit 13, and the determination unit 14 are examples of an acquisition means, a specifying means, a calculation means, and a determination means in order.

The storage unit 15 is, for example, a storage device such as a random access memory (RAM) 903 or a hard disk 904 described later with reference to FIG. 9. The storage unit 15 stores login information 151, the operation log 200, a non-operation period 153, scheduled working hours 154, working hours 155, a working time calculation standard 156, a noise specifying condition 157, and a warning standard 158. These pieces of information stored in the storage unit 15 will be described later.

The acquisition unit 11 acquires the operation log 200 from each terminal 20. The operation log 200 may be acquired after a login operation to the electronic medical record system 21 via the terminal 20 is performed. As described above, since there is a possibility that a plurality of medical workers may use the individual terminal 20 in cooperation, by acquiring the operation log 200 after logging in to the electronic medical record system 21, the operation log 200 acquired from the terminal 20 can be accurately associated with the ID of the medical worker. Alternatively, the operation log 200 may be periodically acquired from the terminal 20, or may be collectively acquired from the terminal 20 when a specific event is detected in the management terminal 22 or the terminal 20. The terminal 20 may hold the login information 151 for the electronic medical record system 21, and the acquisition unit 11 may acquire the login information 151 held in the terminal 20. The acquisition unit 11 stores the acquired login information 151 and operation log 200 in the storage unit 15.

The login information 151 indicates a login operation performed by the medical worker at least one of when starting to use the terminal 20 and when starting to access the electronic medical record system 21 from the terminal 20. The login information 151 includes the ID of the medical worker input by the medical worker in the login operation, information for identifying the terminal 20 that has performed the login operation, and the time when the login operation has been performed.

The operation log 200 indicates an operation content for the terminal 20. The operation log 200 is associated with the ID of the medical worker included in the login information 151. This association is performed by processing with reference to a login time included in the login information 151 and information for identifying the terminal 20 that has performed the login operation, and information for identifying the terminal 20 included in the operation log 200 that occurs after login and an occurrence time of each operation (operation start time, operation end time, and the like).

Figure 2:
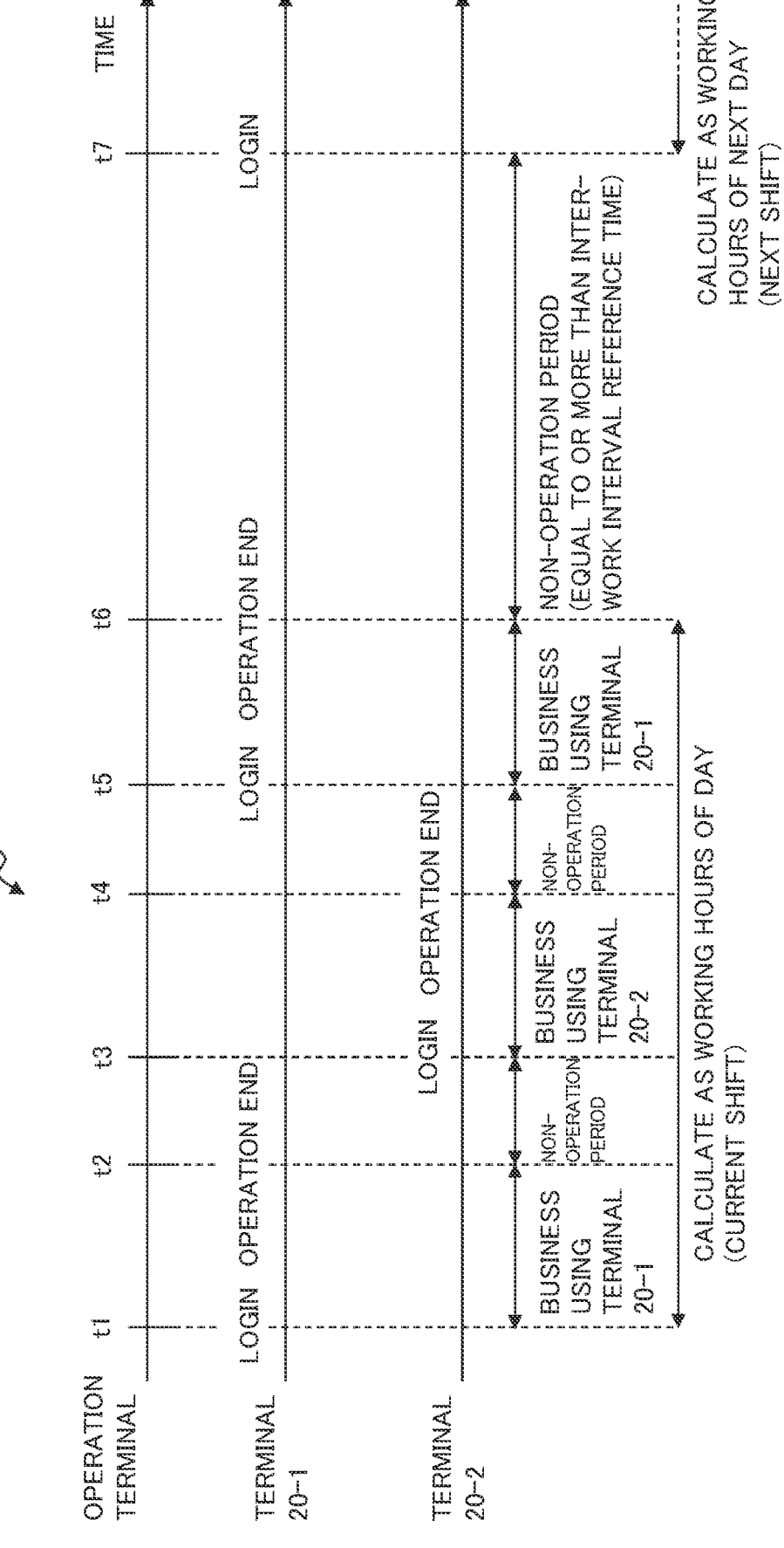
FIG. 2 is a diagram schematically illustrating login information and an operation log in the present disclosure.

FIG. 2 is a diagram schematically illustrating the login information 151 and the operation log 200 according to the present example embodiment. The login information 151 and the operation log 200 illustrated in FIG. 2 indicate a history of operation of the terminal 20-1 and the terminal 20-2 by a certain medical worker during work on a certain day. The work management device 10 according to the present example embodiment uses the login information 151 and the operation log 200 illustrated in FIG. 2 for each medical worker.

According to the login information 151 and the operation log 200 illustrated in FIG. 2, the medical worker performs a login operation on the terminal 20-1 (first terminal) at a time t1 and then performs business using the terminal 20-1 until a time t2. The time t2 represents the end time of the operation in the operation log 200 using the terminal 20-1. The operation performed at the time t2 may be a logoff operation or may be an operation different from the logoff operation.

Figure 3:
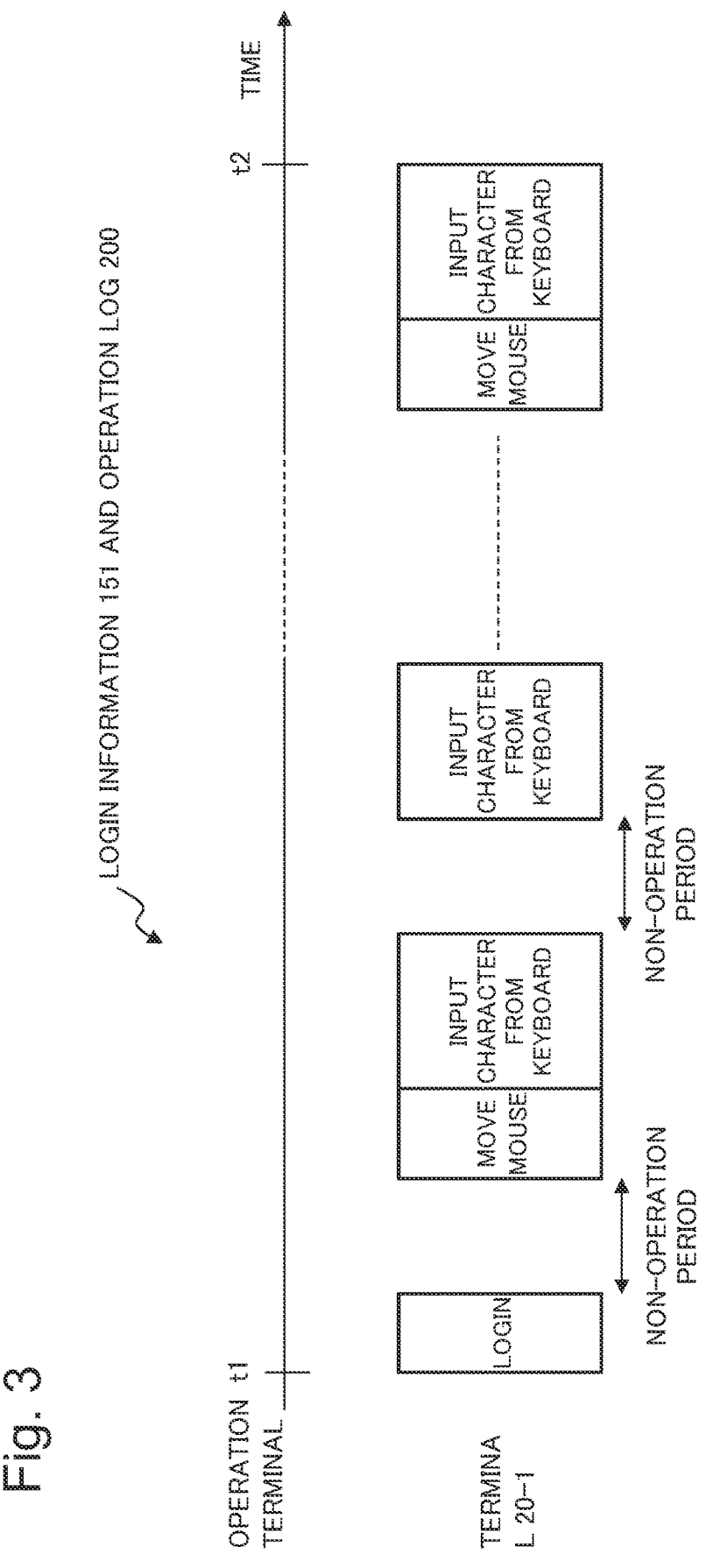
FIG. 3 is a diagram illustrating the login information and the operation log in the present disclosure in more detail.

FIG. 3 is a diagram illustrating the login information 151 and the operation log 200 in a period from the time t1 to the time t2 illustrated in FIG. 2 in more detail.

The login information 151 and the operation log 200 illustrated in FIG. 3 indicate time series in which operations such as login operation, mouse movement, and character input from a keyboard occur. As illustrated in FIG. 3, in the period from time t1 to time t2, there are a plurality of operation logs 200 such as login operation, mouse movement, and character input from a keyboard. In the period from time t1 to time t2, there are a period in which the operation using the terminal 20-1 is performed and a period in which no operation is performed (non-operation period). The period during which the operation using the terminal 20-1 is performed is, for example, the period from the start time to the end time of the login operation. In a case where the start time and the end time of different types of operation have a predetermined relationship, the period during which the operation is performed may be specified based on the start time and the end time of each operation log 200. For example, in the example of FIG. 3, the end time of the mouse movement operation and the start time of the character input operation from the keyboard are continuous. In such a case, a period from the operation start time of the mouse movement to the end time of the operation with the character input from the keyboard can also be specified as the period in which the operation is performed. The predetermined relationship is, for example, a case where the start time of another operation overlaps between the start time and the end time of a certain operation, a case where the end time of a certain operation is continuous with the start time of another operation, or the like. The non-operation period is information indicating the period during which no operation is performed by the terminal 20-1. In the example of FIG. 3, there is no history that the terminal 20-1 is operated between the end time of the login operation and the start time of the mouse movement operation. Therefore, such a period is specified as the non-operation period. The non-operation period can be specified, for example, by obtaining a period from an end time of a certain operation to a start time of another operation performed next to the certain operation.

According to the login information 151 and the operation log 200 illustrated in FIG. 2, the medical worker performs a login operation using the terminal 20-2 (second terminal) at a time t3 after the time t2, and then performs business using the terminal 20-2 until a time t4 after the time t3. The terminal 20-1 and the terminal 20-2 are, for example, terminals installed in different examination rooms. In the example illustrated in FIG. 2, the medical worker moves from the examination room in which the terminal 20-1 is installed to the examination room in which the terminal 20-2 is installed between the time t2 and the time t3, and starts the business using the terminal 20-2 at the time t3. Therefore, in the period from time the t2 to the time t3, there is no operation log 200 of the terminal 20-1 associated with this medical worker. Therefore, the period from the time t2 to the time t3 for the medical worker is the non-operation period during which the terminal 20-1 is not operated.

According to the login information 151 and the operation log 200 illustrated in FIG. 2, the medical worker performs a login operation on the terminal 20-1 at a time t5 after the time t4, and then performs business using the terminal 20-1 until time t6 after time t5. In the example illustrated in FIG. 2, the medical worker returns from the examination room where the terminal 20-2 is installed to the examination room where the terminal 20-1 is installed from time t4 to time t5, and starts the business using the terminal 20-1 at the time t5. Therefore, in the period from the time t4 to the time t5, there is no operation log 200 of the terminal 20-2 associated with this medical worker. Therefore, the period from the time t4 to the time t5 for the medical worker is the non-operation period during which the terminal 20-2 is not operated.

According to the login information 151 and the operation log 200 illustrated in FIG. 2, the medical worker performs a login operation on the terminal 20-1 at a time t7 after a time t6. Therefore, in a period from the time t6 to the time t7, there is no operation log 200 of the terminal 20-1 associated with this medical worker. Similarly, in the terminal 20-2, there is no operation log 200 associated with this medical worker. Therefore, the period from the time t6 to the time t7 is the non-operation period during which the medical worker does not operate the terminal 20-1 and the terminal 20-2. In the example illustrated in FIG. 2, the non-operation period from the time t6 to the time t7 is longer than an inter-work interval reference time. The inter-work interval reference time is, for example, a minimum time required to be spaced from the end of work on a certain day to the start of work on the next day, and is, for example, 10 hours. The inter-work interval reference time may be arbitrarily set by an administrator of the system. At the time of setting, different inter-work interval reference times may be set for each individual medical worker.

The specifying unit 12 specifies the non-operation period 153 of the terminal 20 illustrated in FIGS. 2 and 3 from the login information 151 and the operation log 200, and stores the specified non-operation period 153 in the storage unit 15. For example, in the example illustrated in FIG. 2, the specifying unit 12 specifies the period from time the t2 to the time t3, the period from the time t4 to the time t5, and the period from the time t6 to the time t7 as the non-operation period 153. In the example illustrated in FIG. 2, it is illustrated that the business is performed in the period from the time t1 to the time t2 for simplification of description. However, as in the example illustrated in FIG. 3, the specifying unit 12 specifies the period in which there is no operation log 200 as the non-operation period even in the period from the time t1 to the time t2. The same applies to the period from the time t3 to the time t4 and the period from the time t5 to the time t6 illustrated in FIG. 2.

As described above, when the operation log 200 of the terminal 20-2 (second terminal) is acquired in the non-operation period from the time t2 (first time) to the time t5 (second time) specified based on the operation log 200 of the terminal 20-1 (first terminal), the specifying unit 12 specifies the period from the time t2 to the time t3 (third time) at which the operation log 200 of the terminal 20-2 is acquired as the non-operation period 153 of the terminal 20.

With respect to each non-operation period 153, the calculation unit 13 calculates the working hours 155 of the medical worker so as to include a period satisfying the working time calculation standard 156 in the working hours 155 and not to include a period not satisfying the working time calculation standard 156 in the working hours 155. The working time calculation standard 156 indicates, for example, that the length of the non-operation period 153 is less than the inter-work interval reference time. The calculation unit 13 stores the calculated working hours 155 in the storage unit 15.

In the example illustrated in FIG. 2, for example, since the period from the time t2 to the time t3 and the period from the time t4 to the time t5 are less than the inter-work interval reference time, the calculation unit 13 includes these non-operation periods 153 in the working hours 155. That is, the calculation unit 13 calculates the working hours 155 includ-ing the non-operation period 153 excluding the non-opera-tion period 153 from the time t6 to the time t7 that is equal to or longer than the inter-work interval reference time illustrated in FIGS. 2 and 3.

Therefore, in the example illustrated in FIG. 2, the cal-culation unit 13 calculates the period from the time t1 when the login is performed in the terminal 20-1 to the time t6 when the last operation is performed using the terminal 20-1 as the working hours 155 of the day (current shift). That is, the calculation unit 13 sets the time t6, which is the start time of the non-operation period 153 equal to or longer than the inter-work interval reference time, as the work end time. Then, the calculation unit 13 calculates a period starting from the time t7 when the login operation is performed on the terminal 20-1 after the non-operation period 153 that is equal to or longer than the inter-work interval reference time as the working hours 155 of the next day (next shift).

In a state where the terminal 20 is not used and the logoff operation is not performed, the specifying unit 12 may determine that the operation log 200 recorded due to, for example, occurrence of an earthquake or erroneous touching of a mouse by someone is noise, and set the period of the operation log 200 as the non-operation period 153. The noise is the operation log 200 generated when the terminal 20 is operated for some reason even though the medical worker is not performing business using the terminal 20. The noise specifying condition 157 (predetermined operation condi-tion) for specifying such noise may be provided. Then, the non-operation period may be specified on the assumption that the operation is not performed in the operation log 200 satisfying the noise specifying condition 157. That is, the operation log 200 satisfying the noise specifying condition 157 is treated as the operation log 200 not existing. The noise specifying condition 157 includes, for example, the following conditions, but the conditions included in the noise specifying condition 157 are not limited to the fol-lowing conditions.

(1) A length of the period from a start time to an end time of an operation included in the operation log 200 is shorter than a first threshold (for example, 5 seconds).

(2) The operation logs 200 are acquired or not acquired in a predetermined order (for example, the mouse is moving without input to the keyboard).

(3) Based on the operation start time and the operation end time included in the operation log 200, a first non-operation period continued until the operation start time is longer than a second threshold (for example, 4 hours), and a second non-operation period continued after the operation end time is longer than a third threshold (for example, 1 hour). The second threshold and the third threshold are arbitrarily set, and may be the same value, for example.

(4) The operation log 200 is generated at a time not included in the scheduled working hours 154 indicating the work schedule of the medical worker.

The noise specifying condition 157 may include all of the conditions described above, or only one of the conditions may be set. Some conditions may be combined.

The calculation unit 13 also calculates a difference between the working hours 155 of the medical worker calculated as described above and the scheduled working hours 154 related to the medical worker. The scheduled working hours 154 is, for example, a shift table including a scheduled work start time, a scheduled work end time, a break time, and the like. The scheduled working hours 154 may indicate, for example, a length of the scheduled work-ing hours excluding the break time. The difference between the working hours 155 and the scheduled working hours 154 represents overtime working hours.

The determination unit 14 determines whether the difference between the working hours 155 and the scheduled working hours calculated by the calculation unit 13 as described above satisfies the warning standard 158. When the difference satisfies the warning standard 158, the determination unit 14 outputs a warning to, for example, the management terminal 22.

The warning standard 158 indicates, for example, that the overtime working hours per a predetermined period (one day, one week, one month, or the like) indicated by the difference exceeds an upper limit value of the overtime working hours per the predetermined period. The upper limit value is a value determined by, for example, a law or a regulation regarding working conditions of a medical institution. The upper limit value may be set to an arbitrary value by an administrator of the system or an individual user.

Next, an operation (processing) of the work management device 10 according to the present example embodiment will be described in detail with reference to a flowchart of FIG. 4.

The acquisition unit 11 acquires the operation log 200 collected by each terminal from each terminal 20, acquires the login information 151 regarding each medical worker from the electronic medical record system 21, and stores the acquired login information 151 and operation log 200 in the storage unit 15 (step S101). The specifying unit 12 specifies the period in which there is no operation log 200 as the non-operation period 153 (step S102). The specifying unit 12 determines whether the operation log 200 satisfies the noise specifying condition 157 (step S103).

When the operation log 200 does not satisfy the noise specifying condition 157 (No in step S104), the processing proceeds to step S106. Meanwhile, when the operation log 200 satisfies the noise specifying condition 157 (Yes in step S104), the specifying unit 12 includes the period indicated by the operation log 200 in the non-operation period 153 (step S105).

With respect to each non-operation period 153, the calculation unit 13 calculates the working hours 155 so that the period satisfying the working time calculation standard 156 is included in the working hours 155 (step S106-1). With respect to each non-operation period 153, the calculation unit 13 calculates the working hours 155 so as not to include the period not satisfying the working time calculation standard 156 in the working hours 155 (step S106-2). The calculation unit 13 calculates the difference between the working hours 155 and the scheduled working hours 154, and the determination unit 14 determines whether the calculated difference satisfies the warning standard 158 (step S107).

When the difference between the calculated working hours 155 and the scheduled working hours 154 does not satisfy the warning standard 158 (No in step S108), the entire processing ends. In a case where the difference between the calculated working hours 155 and the scheduled working hours 154 satisfies the warning standard 158 (Yes in step S108), the determination unit 14 outputs a warning regarding the working hours 155 of the medical worker to the management terminal 22 (S109), and the entire processing is terminated.

The work management device 10 according to the present example embodiment can accurately and easily grasp the working hours of the worker (medical worker) even when an input operation for grasping the end time of work such as a logoff operation is not performed on the terminal 20. The reason is that the work management device 10 specifies the non-operation period 153 from the login information 151 and the operation log 200 related to the terminal 20 and determines whether the non-operation period is included in the working hours according to the length of the non-operation period 153.

Hereinafter, effects achieved by the work management device 10 according to the present example embodiment will be described in detail.

The work management device 10 according to the present example embodiment calculates the working hours 155 including the non-operation period 153 excluding the non-operation period that is equal to or longer than the inter-work interval reference time from the login information 151 to the electronic medical record system 21 and the operation log 200 related to the terminal 20. Such calculation of the working hours 155 is based on the fact that it is required to set an interval equal to or longer than the inter-work interval reference time between the work on the day (current shift) and the work on the next day (next shift), and the non-operation period that does not satisfy the inter-work interval reference time even when the non-operation state continues to some extent can be regarded as the working hours. When the working hours 155 are calculated in this manner, the information regarding the input operation for grasping the end time of work such as the logoff operation is not required. Therefore, the work management device 10 can accurately and easily grasp the working hours of the worker even when the input operation for grasping the work end time such as the logoff operation is not performed on the terminal 20.

The work management device 10 according to the present example embodiment calculates the difference between the calculated working hours 155 and the scheduled working hours 154, and outputs a warning to the management terminal 22 when the difference satisfies the warning standard 158. As a result, the work management device can support appropriate management of working hours so as not to impair health of workers.

The work management device 10 according to the present example embodiment considers the operation log 200, which is included in the operation log 200 and satisfies the noise specifying condition 157 such as a short-term operation in which the mouse has moved without performing the input to the keyboard, as noise caused by an earthquake or the like, and includes the operation log in the non-operation period 153. As a result, since the work management device 10 avoids erroneously specifying the non-operation period 153 due to the occurrence of an earthquake or the like, calculation accuracy of the working hours can be improved.

The work management device 10 according to the present example embodiment uses, as the noise specifying condition 157, that the operation log 200 is acquired in a predetermined order or is not acquired. Based on the operation start time and the operation end time included in the operation log 200, the work management device 10 also uses, as the noise specifying condition 157, the fact that the non-operation period 153 continued until the operation start time is longer than the second threshold and the non-operation period 153 continued after the operation end time is longer than the third threshold. The work management device 10 also uses, as the noise specifying condition 157, the occurrence of the operation log 200 at a time not included in the scheduled working hours 154. As a result, the work management device 10 can determine whether the operation log 200 is noise with high accuracy.

In the work management device 10 according to the present example embodiment, the acquisition unit 11 may acquire the prescription time at which the medical worker has prescribed the prescription, for example, from the electronic medical record system 21. In this case, the calculation unit 13 may calculate the working hours 155 based on the prescription time and the operation log 200 of the terminal 20. In this case, the calculation unit 13 compares the time t6 exemplified in FIG. 2 with the last prescription time of the medical worker at work on that day. In a case where the prescription time is later than the time t6, for example, the calculation unit 13 may calculate the working hours 155 by replacing a period not included in the working hours 155 with a period from the prescription time to the time t7 instead of the non-operation period 153 from the time t6 to the time t7. Then, when the prescription time is before the time t6, the calculation unit 13 may calculate the working hours 155 by setting a period not included in the working hours 155 as the non-operation period 153 from the time t6 to the time t7. In this case, since the work management device 10 calculates the working hours 155 in consideration of the prescription time, it is possible to further increase the accuracy of calculating the working hours.

Although the work management device 10 according to the present example embodiment has been described with the electronic medical record system 21 as an example, the working hours of the medical worker may be managed in cooperation with a system or an application other than the electronic medical record system. The work management device 10 is not limited to the medical worker, and may manage the working hours of workers in other job types and industry types. For example, instead of the electronic medical record system, the work management device 10 may cooperate with software that supports design such as CAD (Computer Aided Design), a business support system that performs order management, or the like. The work management device 10 is not limited to one system, and may cooperate with a plurality of systems. In such a case, the work management device 10 may associate the ID of each system with information for identifying the worker, and may associate the operation log 200 obtained after login of each system with the information for identifying the worker.

Modification Example of First Example Embodiment

Figure 5:
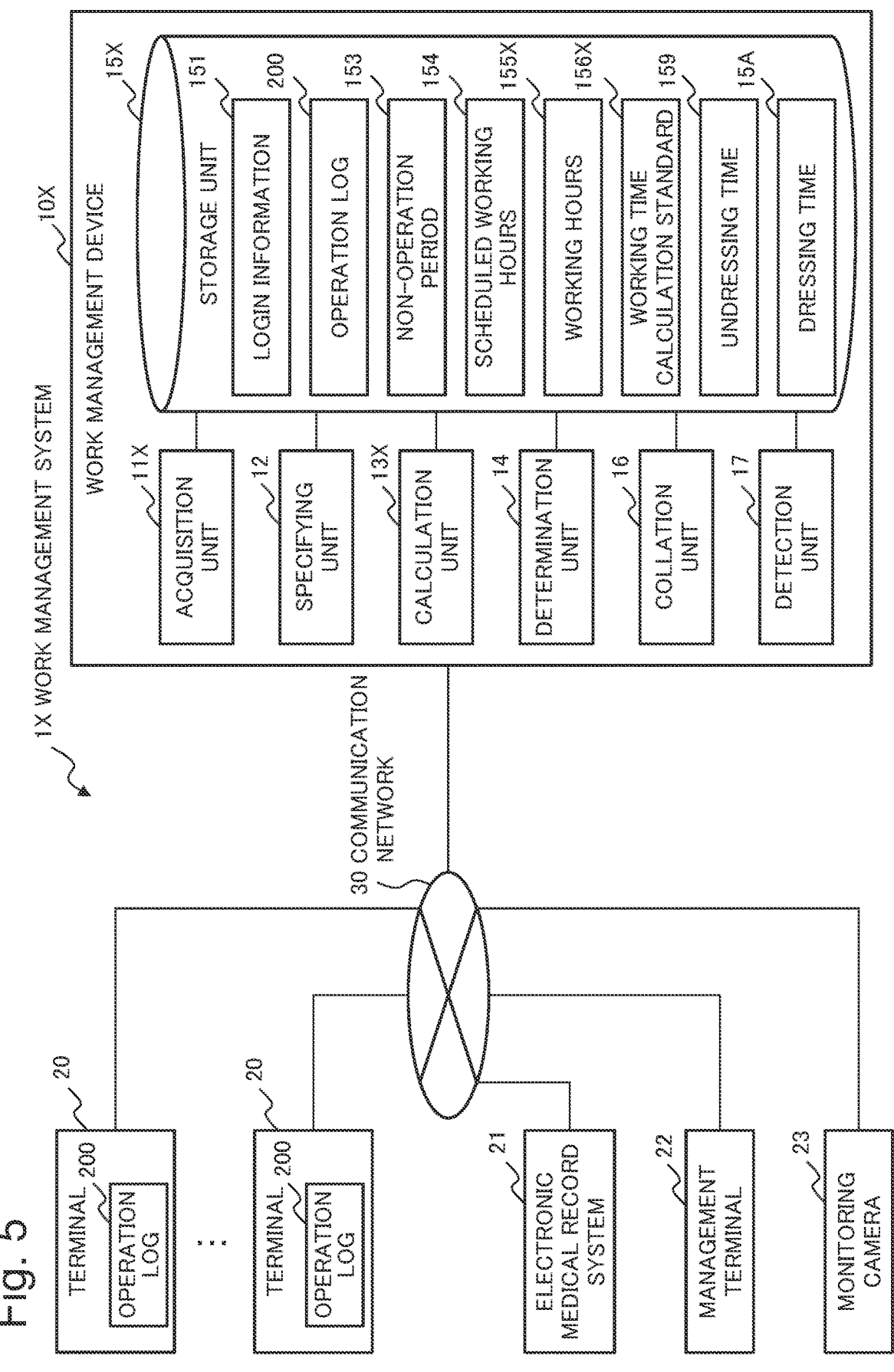
FIG. 5 is a block diagram illustrating a configuration of a work management system according to a modification example of the present disclosure.

FIG. 5 is a block diagram illustrating a configuration of a work management system 1X according to a modification example of the first example embodiment of the present disclosure. In the present modification example, components having functions similar to those in the first example embodiment are denoted by the same reference numerals as those of the components of the work management system 1 illustrated in FIG. 1, and a detailed description thereof will be omitted.

The work management system 1X roughly includes a work management device 10X, one or more terminals 20, an electronic medical record system 21, a management terminal 22, and a monitoring camera 23. The work management device 10X, the terminal 20, the electronic medical record system 21, the management terminal 22, and the monitoring camera 23 are communicably connected via a communication network 30.

The monitoring camera 23 is installed, for example, near an entrance of a dressing room in a medical institution, and captures an image of a medical worker entering the dressing room or leaving the dressing room. However, it is assumed that the monitoring camera 23 does not image the inside of the dressing room.

The work management device 10X includes an acquisition unit 11X, a calculation unit 13X, a storage unit 15X, a collation unit 16, and a detection unit 17 as components different from those of the work management device 10 according to the first example embodiment. The acquisition unit 11X, the calculation unit 13X, the collation unit 16, and the detection unit 17 are examples of an acquisition means, a calculation means, a collation means, and a detection means in order. The storage unit 15X of the work management device 10X stores working hours 155X, a working time calculation standard 156X, an undressing time 159, and a dressing time 15A as information different from the information stored in the storage unit 15 according to the first example embodiment. These pieces of information stored in the storage unit 15X will be described later.

The acquisition unit 11X acquires the captured image of the medical worker from the monitoring camera 23. Note that the captured image includes an imaging time.

The collation unit 16 collates the captured image of the medical worker with the image for specifying the medical worker using, for example, an existing image recognition technology. For example, the collation unit 16 identifies the medical worker by performing face authentication on the medical worker included in the captured image. Alternatively, the collation unit 16 may identify the medical worker included in the captured image by extracting a name written in a name tag of the medical worker included in the captured image.

The detection unit 17 analyzes the captured image of the specified medical worker whether the clothing of the medical worker is clothing (white clothing, uniform, or the like) worn during work using, for example, the existing image recognition technology. Then, for example, the detection unit 17 detects, as the undressing time 159 at which the medical worker takes off the clothing worn during work, a time at which it is imaged that the clothing when the medical worker enters the dressing room is the clothing worn during work and the clothing when the medical worker leaves the dressing room is plain clothes. The detection unit 17 stores the detected undressing time 159 in the storage unit 15X.

The calculation unit 13X calculates the working hours 155X based on the undressing time 159, the operation log 200, and the working time calculation standard 156X. For example, in the example illustrated in FIG. 2 described above, the calculation unit 13X compares the time t6 at which the operation by the medical worker indicated by the operation log 200 ends with the undressing time 159. However, it is assumed that a difference between the time t6 and the undressing time 159 is equal to or less than a predetermined threshold (for example, 10 minutes).

In a case where the undressing time 159 is later than the time t6, it is considered that after performing the last operation using the terminal 20-1 at the time t6, the medical worker changes into plain clothes at the undressing time 159 and finishes the work on that day. In this case, in accordance with the working time calculation standard 156X, the calculation unit 13X calculates the working hours 155X by replacing, for example, the period not included in the working hours 155X with a period from the undressing time 159 to the time t7 instead of the non-operation period 153 from the time t6 to the time t7.

In a case where the undressing time 159 is before the time t6, it is considered that the medical worker changes into plain clothes at the undressing time 159, for example, notices that he/she has left his/her business, performs the last operation using the terminal 20-1 at the time t6, and then ends the work on that day. In this case, the calculation unit 13X calculates the working hours 155X without including the non-operation period 153 from the time t6 to the time t7 in accordance with the working time calculation standard 156X as in the first example embodiment.

The detection unit 17 may detect the dressing time 15A at which the medical worker changes from the plain clothes to the clothes worn during work when the medical worker goes to work at the medical institution. In this case, in the example illustrated in FIG. 2, in a case where the dressing time 15A is before the time t7, the calculation unit 13X may calculate the working hours 155X by, for example, replacing the time at which the next day's work starts with the dressing time 15A from the time t7.

The work management device 10X according to the present modification example can accurately and easily grasp the working hours of the worker (medical worker) even when an input operation for grasping the end time of work such as a logoff operation is not performed on the terminal 20. The reason is as described in the first example embodiment.

Since the work management device 10X according to the present modification example calculates working hours 155X based on at least one of the undressing time 159 at which the worker takes off the clothes worn during work and the dressing time 15A at which the worker wears the clothes worn during work, it is possible to further improve the accuracy of calculating the working hours.

Second Modification Example of First Example Embodiment

In a second modification example of the first example embodiment, the work management device 10 according to the first example embodiment may include a calculation unit 13Y (not illustrated) that calculates working hours 155 by machine learning instead of the calculation unit 13. In this case, the calculation unit 13Y learns in advance an estimation model for estimating the working hours 155 using, for example, information such as the past login information 151 and the operation log 200. The calculation unit 13Y calculates the working hours 155 using the estimation model based on the login information 151, the operation log 200, and the like to be estimated. The calculation unit 13Y stores the calculated working hours 155 in the storage unit 15. According to such a configuration, the working hours can be calculated by the machine learning method, and the working hours of the worker can be accurately and easily grasped. By outputting the warning by the determination unit 14 to the management terminal 22, it is possible to encourage the administrator to make a decision for appropriately maintaining the working hours of the worker.

Second Example Embodiment

Figure 6:
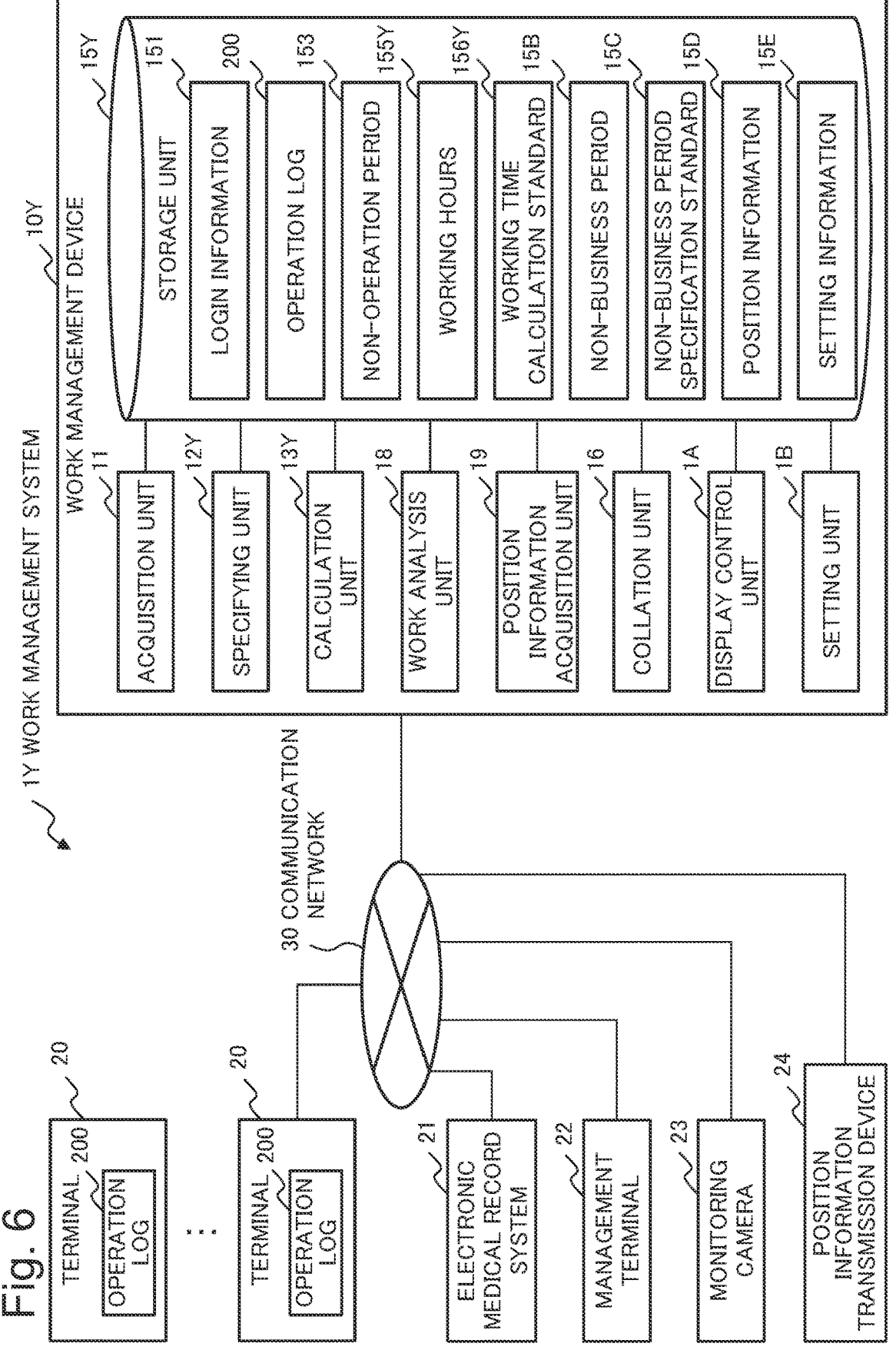
FIG. 6 is a block diagram illustrating a configuration of a work management system according to the present disclosure.

FIG. 6 is a block diagram illustrating a configuration of a work management system 1Y according to a second example embodiment of the present disclosure. In the present example embodiment, components having functions similar to those in the first example embodiment or the modification example of the first example embodiment are denoted by the same reference numerals as the components of the work management system 1 illustrated in FIG. 1 or the work management system 1X illustrated in FIG. 5, and detailed descriptions thereof will be omitted.

The work management system 1Y roughly includes a work management device 10Y, one or more terminals 20, an electronic medical record system 21, a management terminal 22, a monitoring camera 23, and a position information transmission device 24. The work management device 10Y, the terminal 20, the electronic medical record system 21, the management terminal 22, the monitoring camera 23, and the position information transmission device 24 are communicably connected via a communication network 30.

The monitoring camera 23 is installed in various places including, for example, a place where a medical worker performs business, such as an examination room and an operation room, and a place where the medical worker takes a rest, such as a dining room, in a medical institution, and images the medical worker in various places.

The position information transmission device 24 is a device such as a beacon terminal possessed by a medical worker, and transmits position information indicating the position of the medical worker.

The work management device 10Y includes, as components different from the work management device 10 according to the first example embodiment and the work management device 10X according to the modification example of the first example embodiment, a specifying unit 12Y, a calculation unit 13Y, a storage unit 15Y, a work analysis unit 18, a position information acquisition unit 19, a display control unit 1A, and a setting unit 1B. The specifying unit 12Y, the calculation unit 13Y, the work analysis unit 18, the position information acquisition unit 19, the display control unit 1A, and the setting unit 1B are examples of a specifying means, a calculation means, a work analysis means, a position information acquisition means, a display control means, and a setting means. The storage unit 15Y of the work management device 10Y stores, as information different from the information stored in the storage unit 15 according to the first example embodiment and the storage unit 15X according to the modification example of the first example embodiment, working hours 155Y, a working time calculation standard 156Y, a non-business period 15B, a non-business period specification standard 15C, position information 15D, and setting information 15E. These pieces of information stored in the storage unit 15Y will be described later.

The work analysis unit 18 analyzes a work content using the terminal 20 by the medical worker from the operation log 200 of the terminal 20 acquired by the acquisition unit 11. The operation log 200 includes, for example, a uniform resource locator (URL) or the like of an access destination accessed from the terminal 20 via the communication network 30, and the work analysis unit 18 analyzes (extracts) a keyword or the like included in information described in the URL by using, for example, an existing morphological analysis technique, a syntax analysis technique, or the like. The operation log 200 also includes identification information (file name) and the like of a file (data) created by a medical worker, and the work analysis unit 18 analyzes (extracts) a keyword and the like included in a file specified by the identification information.

From the analysis result of the work content using the terminal 20 by the work analysis unit 18, the specifying unit 12Y specifies a non-business period 15B in which work that is not included in the business of the medical worker is being performed in accordance with the non-business period specification standard 15C. The non-business period specification standard 15C represents, for example, whether a keyword or the like included in the analysis result is related to the business of the medical worker. The specifying unit 12Y stores the specified non-business period 15B in the storage unit 15Y.

The position information acquisition unit 19 acquires the position information 15D of the medical worker at each time, and stores the acquired position information 15D in the storage unit 15Y. The position information acquisition unit 19 acquires the position information 15D from the position information transmission device 24, for example. The position information acquisition unit 19 may also acquire the position information 15D of the medical worker indicated by the position of the monitoring camera 23 that has captured the captured image in which the collation results regarding the medical worker by the collation unit 16 match.

The specifying unit 12Y specifies the non-business period 15B from the position information 15D for each time of the medical worker acquired by the position information acquisition unit 19 in accordance with the non-business period specification standard 15C. The non-business period specification standard 15C indicates a place that is not a place where the medical worker performs the business, and defines a rest place such as a dining room as such a place. The period in which the medical worker is in a place other than the place where the medical worker performs the business defined as described above is a period that can be regarded as the non-business period 15B. The specifying unit 12Y stores the specified non-business period 15B in the storage unit 15Y.

The calculation unit 13Y calculates the working hours 155Y of the medical worker excluding the non-business period 15B specified by the specifying unit 12Y as described above, and stores the calculated working hours 155Y in the storage unit 15Y.

The display control unit 1A displays, on the management terminal 22, a menu screen prompting the input of the setting information 15E for setting at least one of the working time calculation standard 156Y and the non-business period specification standard 15C described above. The setting information 15E indicates, for example, a policy of not including an actual period of stay in a place that is not a place where the medical worker performs the business in the working hours 155Y or not including a uniform time (for example, 1 hour) as a break time in the working hours 155Y. Alternatively, in a case where the work content indicated by the analysis result by the work analysis unit 18 indicates, for example, investigation, learning, or the like regarding the trend of the medical technology, the setting information 15E indicates a policy as to whether the working time is treated as the non-business period 15B.

As an example of the menu screen prompting the input of the setting information 15E, the display control unit 1A may display conditions included in the working time calculation standard 156Y and the non-business period specification standard 15C, and may display a screen for selecting validity/invalidity of these conditions. A menu screen for setting (inputting) the working time calculation standard 156Y and the non-business period specification standard 15C themselves may be displayed. For example, a map of the hospital may be displayed on the management terminal 22, and designation of a place on the displayed map may be accepted. Then, the range designated on the map may be set as a place other than the place where the medical worker performs the business. As a result, the non-business period specification standard 15C can be set.

The setting unit 1B receives the setting information 15E input by the administrator or the like of the work management device 10Y via the management terminal 22, and stores the received setting information 15E in the storage unit 15Y. Then, the setting unit 1B sets the working time calculation standard 156Y and the non-business period specification standard 15C based on the setting information 15E.

Next, the operation (processing) of the work management device 10Y according to the present example embodiment will be described in detail with reference to the flowchart of FIG. 7.

The display control unit 1A displays a menu screen prompting the input of the setting information 15E on the management terminal 22 (step S201). The setting unit 1B receives the setting information 15E input via the management terminal 22, and sets the working time calculation standard 156Y and the non-business period specification standard 15C based on the received setting information 15E (step S202).

Figure 4:
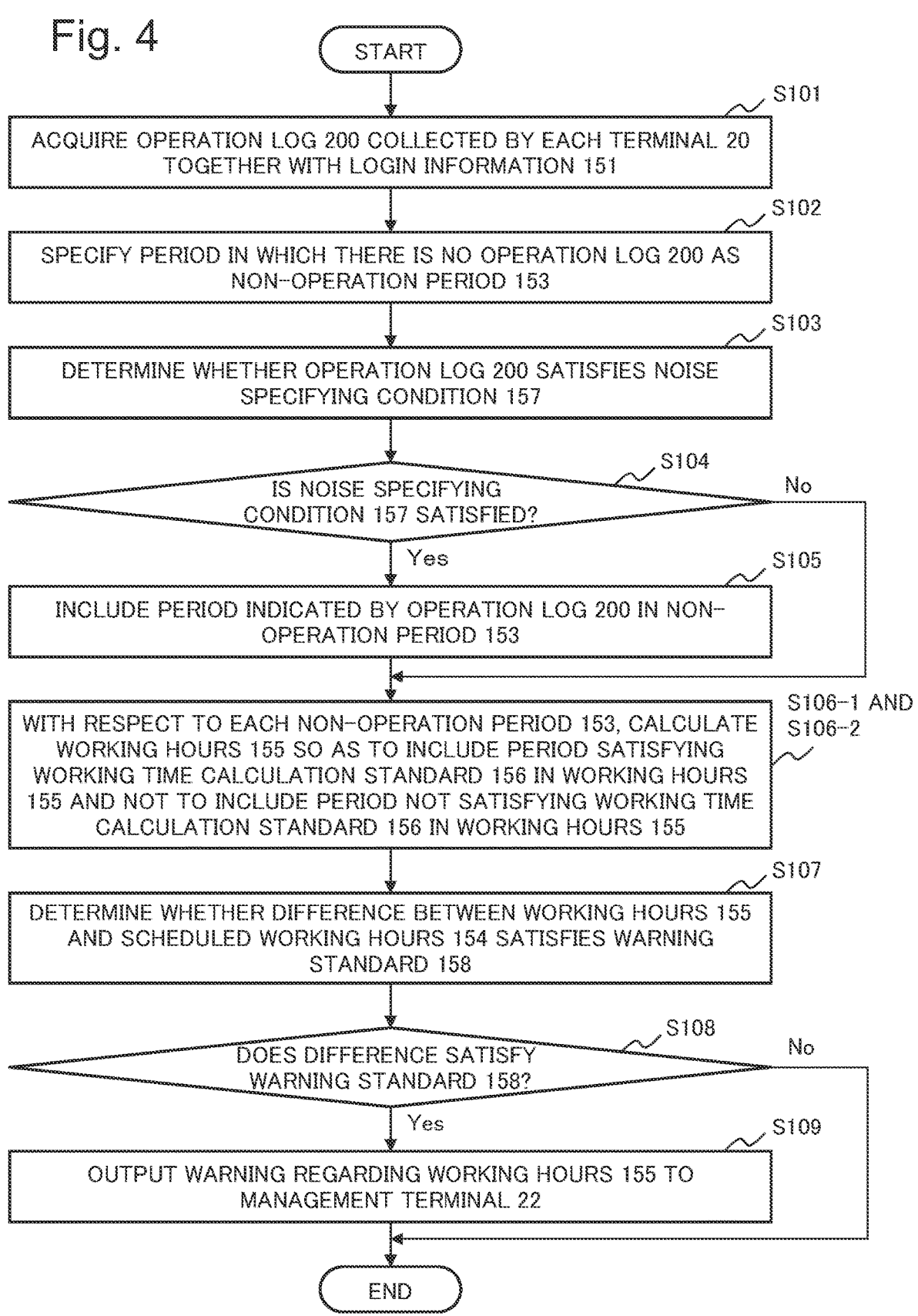
FIG. 4 is a flowchart illustrating an operation of a work management device according to the present disclosure.

The work management device 10Y performs processing similar to steps S101 to S106 illustrated in the flowchart of FIG. 4 (step S203). The work analysis unit 18 analyzes the work content using the terminal 20 at each time from the operation log 200 of the terminal 20 (step S204). The specifying unit 12Y specifies the non-business period 15B based on the analysis result of the work content by the work analysis unit 18 and the non-business period specification standard 15C (step S205).

The position information acquisition unit 19 acquires the position information 15D from the position information transmission device 24 or from the position of the monitoring camera 23 where the collation unit 16 collates the captured image by the monitoring camera 23 with the information for specifying the medical worker and the collation result matches (step S206). The specifying unit 12Y specifies (adds) the non-business period 15B based on the position information 15D acquired by the position information acquisition unit 19 and the non-business period specification standard 15C (step S207). The calculation unit 13Y calculates the working hours 155Y excluding the non-business period 15B specified by the specifying unit 12Y based on the working time calculation standard 156Y, outputs the calculated working hours 155Y to the management terminal 22 (step S208), and ends the entire processing.

The work management device 10Y according to the present example embodiment can accurately and easily grasp the working hours of the worker (medical worker) even when an input operation for grasping the end time of work such as a logoff operation is not performed on the terminal 20. The reason is as described in the first example embodiment.

The work management device 10Y according to the present example embodiment analyzes the work content using the terminal 20 from the operation log 200 of the terminal 20, specifies the non-business period 15B in which work not included in the business is performed from the analysis result, and calculates the working hours 155Y excluding the non-business period 15B. As a result, the work management device 10Y can further increase the accuracy of calculating the working hours.

The work management device 10Y according to the present example embodiment acquires the position information 15D of the worker for each time, specifies the non-business period 15B in which the worker is not at a place where the business is performed from the position information 15D, and calculates the working hours 155Y excluding the non-business period 15B. As a result, the work management device 10Y can further improve the accuracy of calculating the working hours.

In addition to acquiring the position information 15D from the position information transmission device 24, the work management device 10Y according to the present example embodiment acquires the position information 15D from the position of the monitoring camera 23 that has captured the captured image in which the collation between the captured image of the worker and the image for identifying the worker matches. As a result, the work management device 10Y can acquire the position information 15D more reliably even when the worker is in a place where transmission and reception of radio waves related to the position information 15D are difficult or in a place where the monitoring camera 23 is not installed.

The work management device 10Y according to the present example embodiment displays, on the management terminal 22, a menu screen prompting the input of the setting information 15E for setting at least one of the working time calculation standard 156Y and the non-business period specification standard 15C. Then, the work management device 10Y receives the setting information 15E input via the management terminal 22, and sets the working time calculation standard 156Y and the non-business period specification standard 15C based on the setting information 15E. As a result, the work management device 10Y enables the user to flexibly change the calculation policy of the working hours of the worker according to the working environment or the like.

Third Example Embodiment

Figure 8:
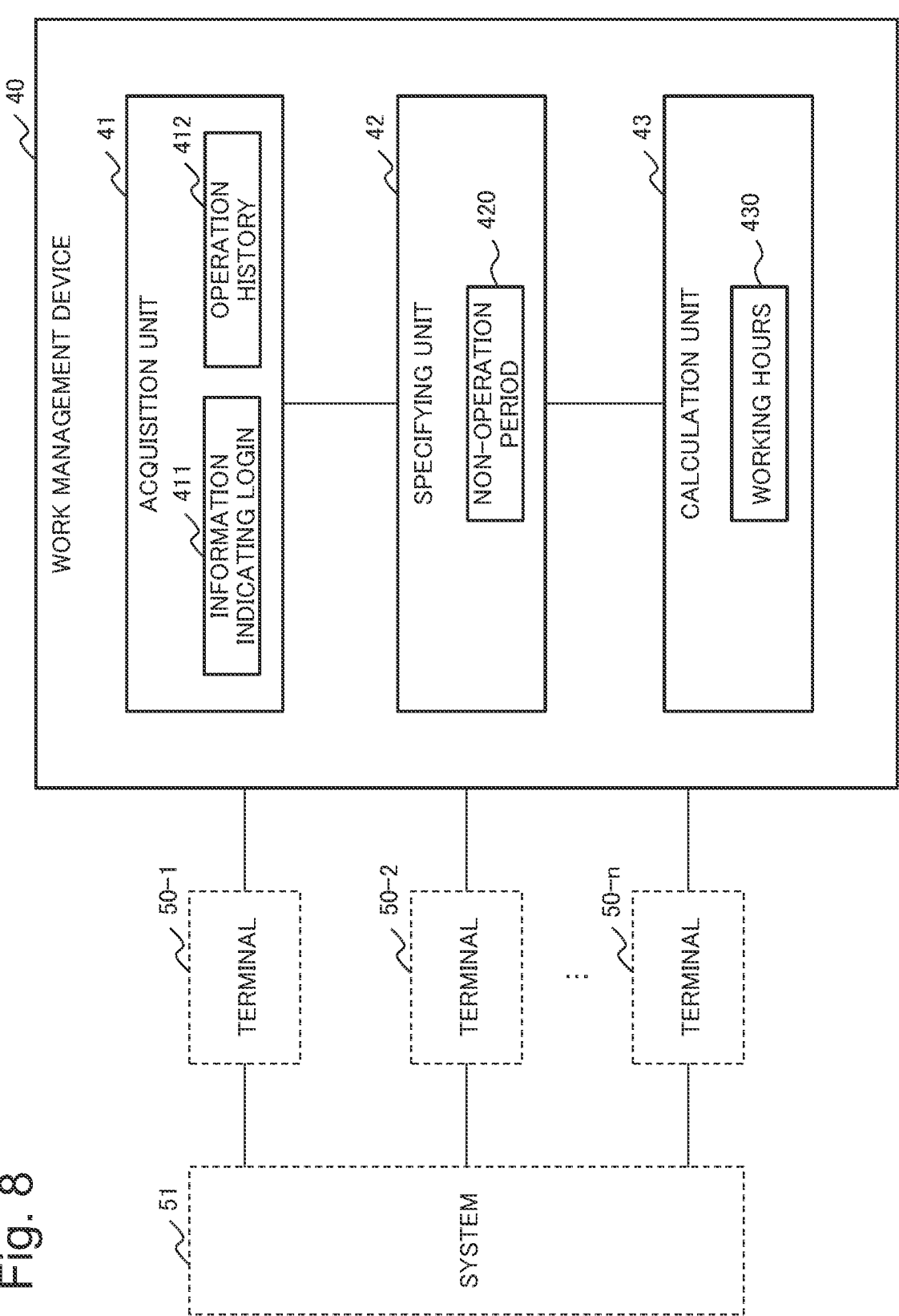
FIG. 8 is a block diagram illustrating a configuration of the work management device according to the present disclosure.

FIG. 8 is a block diagram illustrating a configuration of a work management device 40 according to a third example embodiment of the present disclosure.

The work management device 40 according to the present example embodiment includes an acquisition unit 41, a specifying unit 42, and a calculation unit 43. The acquisition unit 41, the specifying unit 42, and the calculation unit 43 are an example of an acquisition means, a specifying means, and a calculation means in order.

The acquisition unit 41 acquires information 411 indicating login to a system 51 using a terminal 50-1 (first terminal) and an operation history 412 of the terminal 50-1 occurring after login to the system 51. The terminal 50-1 is, for example, a terminal similar to the terminal 20-1 according to the first example embodiment. The system 51 is, for example, a system similar to the electronic medical record system 21 according to the first example embodiment. The information 411 indicating login is, for example, information similar to the login information 151 according to the first example embodiment. The operation history 412 is, for example, information similar to the operation log 200 according to the first example embodiment. The acquisition unit 41 operates similarly to the acquisition unit 11 according to the first example embodiment, for example.

The specifying unit 42 specifies the non-operation period 420 of terminals 50-1 to 50-$n$ (n is an arbitrary natural number) from the operation history 412 of the terminal 50-1. The terminals 50-1 to 50-$n$ are, for example, terminals similar to the terminal 20 according to the first example embodiment. The non-operation period 420 is, for example, information similar to the non-operation period 153 according to the first example embodiment. The specifying unit 42 operates similarly to the specifying unit 12 according to the first example embodiment, for example.

The calculation unit 43 calculates working hours 430 including the non-operation period 420 of the terminals 50-1 to 50-$n$ according to the length of the non-operation period 420 of the terminals 50-1 to 50-$n$. The working hours 430 are, for example, information similar to the working hours 155 according to the first example embodiment. The calculation unit 43 operates similarly to the calculation unit 13 according to the first example embodiment, for example.

The work management device 40 according to the present example embodiment can accurately and easily grasp the working hours of the worker even when an input operation for grasping the work end time such as a logoff operation is not performed on the terminals 50-1 to 50-$n$. This is because the work management device 40 specifies the non-operation period 420 from the information 411 indicating the login related to the terminal 50-1 and the operation history 412, and determines whether the non-operation period 420 is included in the working hours 430 according to the length of the non-operation period 420.

(Hardware)

Each unit in the work management device illustrated in FIGS. 1, 5, 6, and 8 in each of the above-described example embodiments can be achieved by dedicated hardware (HW) (electronic circuit). In FIGS. 1, 5, 6, and 8, at least the following configuration can be regarded as a function (processing) unit (software module) of a software program including an instruction executed by a processor.

Acquisition units 11 and 41,
specifying units 12, 12Y, and 42,
calculation units 13, 13X, 13Y, and 43,
determination unit 14,
storage control function in the storage units 15, 15X, and 15Y,
collation unit 16,
detection unit 17,
work analysis unit 18,
position information acquisition unit 19,
display control unit 1A, and
setting unit 1B.

However, the division of each unit illustrated in these drawings is a configuration for convenience of description, and various configurations can be assumed at the time of implementation. An example of a hardware environment in this case will be described with reference to FIG. 9.

FIG. 9 is a diagram for exemplarily describing a configuration of an information processing device 900 (computer) capable of achieving the work management device according to each example embodiment of the present disclosure. That is, FIG. 9 is a configuration of a computer (information processing device) capable of achieving the work management device illustrated in FIGS. 1, 5, 6, and 8, and indicates a hardware environment capable of achieving each function in the above-described example embodiment.

The information processing device 900 illustrated in FIG. 9 includes the following components as constituent elements.

Central processing unit (CPU) 901,
read only memory (ROM) 902,
random access memory (RAM) 903,
hard disk (storage device) 904,
communication interface 905,
bus 906 (communication line),
reader/writer 908 capable of reading and writing data stored in recording medium 907 such as a compact disc read only memory (CD-ROM), and
input/output interface 909 such as a monitor, a speaker, or a keyboard.

That is, the information processing device 900 including the above-described components is a general computer to which these components are connected via the bus 906. The information processing device 900 may include a plurality of CPUs 901 or may include a CPU 901 configured by multiple cores.

Then, the present disclosure described using the above-described example embodiment as an example supplies a computer program capable of achieving the following functions to the information processing device 900 illustrated in FIG. 9. The function is the above-described configuration in the block configuration diagram (FIGS. 1, 5, 6, and 8) referred to in the description of the example embodiment or the function of the flowchart (FIGS. 4 and 7). Thereafter, the present disclosure is achieved by reading, interpreting, and executing the computer program on the CPU 901 of the hardware. The computer program supplied into the device may be stored in a readable/writable volatile memory (RAM 903) or a nonvolatile storage device such as the ROM 902 or the hard disk 904.

In the above case, a general procedure can be adopted at present as a method of supplying the computer program into the hardware. Examples of the procedure include a method of installing the program in the apparatus via various recording media 907 such as a CD-ROM, a method of downloading the program from the outside via a communication line such as the Internet, and the like. In such a case, the present disclosure can be understood to be constituted by a code constituting the computer program or the recording medium 907 storing the code.

The previous description of embodiments is provided to enable a person skilled in the art to make and use the present disclosure. Moreover, various modifications to these example embodiments will be readily apparent to those skilled in the art, and the generic principles and specific examples defined herein may be applied to other embodiments without the use of inventive faculty. Therefore, the present disclosure is not intended to be limited to the example embodiments described herein but is to be accorded the widest scope as defined by the limitations of the claims and equivalents.

Further, it is noted that the inventor's intent is to retain all equivalents of the claimed invention even if the claims are amended during prosecution.

Note that some or all of the above-described example embodiments can also be described as the following Supplementary Notes. However, the present disclosure exemplarily described by the above-described example embodiments is not limited to the following.

(Supplementary Note 1) A work management device including:

an acquisition unit configured to acquire information indicating login to a system using a first terminal and an operation history of the first terminal occurring after login to the system;

a specifying unit configured to specify a non-operation period of a terminal from the operation history of the first terminal; and a calculation unit configured to calculate working hours including the non-operation period of the terminal according to a length of the non-operation period of the terminal.

(Supplementary Note 2) The work management device according to Supplementary Note 1, in which the calculation unit includes a non-operation period of the terminal less than a predetermined length in the working hours.

(Supplementary Note 3) The work management device according to Supplementary Note 1 or 2, in which the calculation unit calculates the working hours based on a login time to the system using the first terminal and the operation history of the first terminal.

(Supplementary Note 4) The work management device according to Supplementary Note 1 or 2, in which the specifying unit specifies a period in which the operation history of the first terminal after login to the system is not obtained as the non-operation period of the terminal.

(Supplementary Note 5) The work management device according to Supplementary Note 1 or 2, in which the acquisition unit acquires information indicating login to the system using a second terminal and an operation history of the second terminal after login to the system, and the specifying unit specifies a non-operation period of the terminal based on the operation history of the first terminal and the operation history of the second terminal.

(Supplementary Note 6) The work management device according to Supplementary Note 5, in which in a case where the operation history of the second terminal is acquired in a non-operation period from a first time to a second time specified based on the operation history of the first terminal, the specifying unit specifies a period from the first time to a third time at which the operation history of the second terminal is acquired as the non-operation period of the terminal.

(Supplementary Note 7) The work management device according to Supplementary Note 1 or 2, in which the specifying unit specifies a period during which an operation satisfying a predetermined operation condition indicated by the operation history of the first terminal is performed as the non-operation period of the terminal.

(Supplementary Note 8) The work management device according to Supplementary Note 7, in which the specifying unit uses, as the predetermined operation condition, a condition that a content of an operation satisfies a predetermined operation content condition and a length of a period in which the operation is performed is shorter than a first threshold.

(Supplementary Note 9) The work management device according to Supplementary Note 8, in which the predetermined operation content condition indicates an operation in which a mouse has moved without performing an input to a keyboard.

(Supplementary Note 10) The work management device according to Supplementary Note 8, in which the specifying unit uses, as the predetermined operation condition, a condition that a non-operation period of the terminal before an operation occurs is longer than a second threshold and a non-operation period of the terminal after an operation occurs is longer than a third threshold.

(Supplementary Note 11) The work management device according to Supplementary Note 8, in which the specifying unit uses, as the predetermined operation condition, occurrence of an operation at a time not included in scheduled working hours.

(Supplementary Note 12) The work management device according to Supplementary Note 1 or 2, in which the system includes an electronic medical record system used by a medical worker.

(Supplementary Note 13) The work management device according to Supplementary Note 1 or 2, in which the calculation unit calculates a difference between the working hours and scheduled working hours, and the work management device further includes a determination unit configured to determine whether the difference satisfies a warning standard and output a warning when the difference satisfies the warning standard.

(Supplementary Note 14) The work management device according to Supplementary Note 12, in which the acquisition unit acquires a prescription time at which the medical worker prescribed a prescription, and the calculation unit calculates the working hours based on the prescription time and the operation history of the first terminal.

(Supplementary Note 15) The work management device according to Supplementary Note 1 or 2, further including:

a collation unit configured to collate a captured image of a worker with an image for identifying the worker; and a detection unit configured to detect, by analyzing the captured image of the identified worker, undressing time at which the worker has undressed clothes worn during work and dressing time at which the worker has worn the clothes worn during work, in which the calculation unit calculates the working hours based on at least one of the undressing time and the dressing time and the operation history of the first terminal.

(Supplementary Note 16) The work management device according to Supplementary Note 1, further including a work analysis unit configured to analyze a work content using the first terminal from the operation history of the first terminal, in which the specifying unit specifies a non-business period in which work not included in business is performed from an analysis result of a work content using the first terminal, and the calculation unit calculates the working hours excluding the non-business period.

(Supplementary note 17) The work management device according to Supplementary Note 1, further including a position information acquisition unit configured to acquire position information of a worker for each time, in which the specifying unit specifies a non-business period during which a worker is not at a place where business is performed from the position information, and the calculation unit calculates the working hours excluding the non-business period.

(Supplementary Note 18) The work management device according to Supplementary Note 17, in which the position information acquisition unit acquires the position information from a position information transmission device possessed by a worker.

(Supplementary Note 19) The work management device according to Supplementary Note 17, further including a collation unit configured to collate a captured image of a worker with an image for identifying the worker, in which the position information acquisition unit acquires the position information from a position of an imaging unit that has captured the captured image matching collation by the collation unit.

(Supplementary Note 20) The work management device according to Supplementary Note 16 or 17, further including:

a display control unit configured to display, on a management terminal, a menu screen prompting an input of setting information for setting at least one of a calculation standard of the working hours by the calculation unit or a specification standard of the non-business period by the specification unit; and a setting unit configured to receive the setting information input via the management terminal and set the calculation standard and the specification standard based on the setting information, in which the calculation unit calculates the working hours using the calculation standard, and the specifying unit specifies the non-business period using the specification standard.

(Supplementary Note 21) A work management method executed by an information processing device, the method including:

acquiring information indicating login to a system using a first terminal and an operation history of the first terminal occurring after login to the system;

specifying a non-operation period of a terminal from the operation history of the first terminal; and calculating working hours including the non-operation period of the terminal according to a length of the non-operation period of the terminal.

(Supplement Note 22) A non-transitory recording medium storing a program for causing a computer to execute:

an acquisition process of acquiring information indicating login to a system using a first terminal and an operation history of the first terminal occurring after login to the system;

a specifying process of specifying a non-operation period of a terminal from the operation history of the first terminal; and a calculation process of calculating working hours including the non-operation period of the terminal according to a length of the non-operation period of the terminal.

(Supplement Note 23) The work management device according to Supplementary Note 1, further including a determination unit configured to determine whether a difference between the working hours and scheduled working hours satisfies a warning standard, in which the calculation unit calculates the working hours by using an estimation model by machine learning, and the determination unit outputs a warning used for decision making regarding the working hours when the difference satisfies the warning standard.

The invention claimed is:

1. A work management device comprising:
a memory storing instructions; and
a processor connected to the memory and configured to execute the instructions to:
acquire information indicating login to a system using a first terminal and an operation history of the first terminal occurring after login to the system;
specify a non-operation period of a terminal from the operation history of the first terminal;
collate captured images of a worker with an image for identifying the worker;
detect, by analyzing the captured images of the identified worker, undressing time at which the worker has removed clothes worn during work and dressing time at which the worker has worn the clothes worn during work;
obtain first position information of the worker based on a position of a monitoring camera that has captured at least one of the captured images;
obtain second position information of the worker based on position information transmitted by a beacon terminal associated with the worker;

identify a time period in which the worker is outside of a specified area based on the first position information and the second position information; and calculate working hours including the non-operation period of the terminal according to a length of the non-operation period of the terminal, and excluding the time period in which the worker is outside of the specified area.

2. The work management device according to claim 1, wherein the processor is configured to execute the instructions to include a non-operation period of the terminal that is less than a predetermined length in the working hours.

3. The work management device according to claim 1, wherein the processor is configured to execute the instructions to calculate the working hours based on a login time to the system using the first terminal and the operation history of the first terminal.

4. The work management device according to claim 1, wherein the processor is configured to execute the instructions to specify a period in which the operation history of the first terminal after login to the system is not obtained as the non-operation period of the terminal.

5. The work management device according to claim 1, wherein the processor is configured to execute the instructions to acquire information indicating login to the system using a second terminal and an operation history of the second terminal after login to the system, and specify a non-operation period of the terminal based on the operation history of the first terminal and the operation history of the second terminal.

6. The work management device according to claim 5, wherein the processor is configured to execute the instructions to specify, in a case where the operation history of the second terminal is acquired in a non-operation period from a first time to a second time specified based on the operation history of the first terminal, a period from the first time to a third time at which the operation history of the second terminal is acquired as the non-operation period of the terminal.

7. The work management device according to claim 1, wherein the processor is configured to execute the instructions to specify a period during which an operation satisfying a predetermined operation condition indicated by the operation history of the first terminal is performed as the non-operation period of the terminal.

8. The work management device according to claim 1, wherein the processor is configured to execute the instructions to include an electronic medical record system used by a medical worker.

9. The work management device according to claim 1, wherein the processor is configured to execute the instructions to calculate the working hours by using an estimation model by machine learning, determine whether a difference between the working hours and scheduled working hours satisfies a warning standard, and output, when the difference satisfies the warning standard, a warning used for decision making regarding the working hours.

10. A work management method executed by an information processing device, the work management method comprising:

acquiring information indicating login to a system using a first terminal and an operation history of the first terminal occurring after login to the system;

specifying a non-operation period of a terminal from the operation history of the first terminal;

collating captured images of a worker with an image for identifying the worker;

detecting, by analyzing the captured images of the identified worker, undressing time at which the worker has removed clothes worn during work and dressing time at which the worker has worn the clothes worn during work;

obtaining first position information of the worker based on a position of a monitoring camera that has captured at least one of the captured images;

obtaining second position information of the worker based on position information transmitted by a beacon terminal associated with the worker;

identifying a time period in which the worker is outside of a specified area based on the first position information and the second position information; and calculating working hours including the non-operation period of the terminal according to a length of the non-operation period of the terminal, and excluding the time period in which the worker is outside of the specified area.

11. A non-transitory recording medium storing a program for causing a computer to execute:

an acquisition process of acquiring information indicating login to a system using a first terminal and an operation history of the first terminal occurring after login to the system;

a specifying process of specifying a non-operation period of a terminal from the operation history of the first terminal;

a collation process of collating captured images of a worker with an image for identifying the worker;

a detection process of detecting, by analyzing the captured images of the identified worker, undressing time at which the worker has removed clothes worn during work and dressing time at which the worker has worn the clothes worn during work;

a first obtaining process of obtaining first position information of the worker based on a position of a monitoring camera that has captured at least one of the captured images;

a second obtaining process of obtaining second position information of the worker based on position information transmitted by a beacon terminal associated with the worker;

an identification process of identifying a time period in which the worker is outside of a specified area based on the first position information and the second position information; and a calculation process of calculating working hours including the non-operation period of the terminal according to a length of the non-operation period of the terminal, and excluding the time period in which the worker is outside of the specified area.

* * * * *